(12) United States Patent
Lawson, Jr. et al.

(10) Patent No.: US 12,161,769 B1
(45) Date of Patent: Dec. 10, 2024

(54) MOBILE STERILIZATION UNIT

(71) Applicant: METRANSPORT, INC., Phoenix, AZ (US)

(72) Inventors: William M. Lawson, Jr., Phoenix, AZ (US); Antony S. Wilkie, Jr., Phoenix, AZ (US)

(73) Assignee: METRANSPORT, INC., Phoenix, AZ (US)

( * ) Notice: Subject to any disclaimer, the term of this patent is extended or adjusted under 35 U.S.C. 154(b) by 374 days.

(21) Appl. No.: 17/829,290

(22) Filed: May 31, 2022

Related U.S. Application Data

(60) Provisional application No. 63/194,853, filed on May 28, 2021.

(51) Int. Cl.
*A61L 2/10* (2006.01)

(52) U.S. Cl.
CPC ............. *A61L 2/10* (2013.01); *A61L 2202/11* (2013.01); *A61L 2202/16* (2013.01); *A61L 2202/25* (2013.01)

(58) Field of Classification Search
CPC .... A61L 2/10; A61L 2202/11; A61L 2202/16; A61L 2202/25
USPC ............................. 250/454.11, 455.11, 504 R
See application file for complete search history.

(56) References Cited

U.S. PATENT DOCUMENTS

| | | | |
|---|---|---|---|
| 6,631,925 B1 | 10/2003 | Lawson, Jr. | |
| D491,615 S | 6/2004 | Lawson, Jr. | |
| 6,860,512 B2 | 3/2005 | Lawson, Jr. | |
| 8,029,739 B2 | 10/2011 | Field et al. | |
| 8,112,841 B2 | 2/2012 | Garcia et al. | |
| 8,431,075 B2 * | 4/2013 | Davis | A61L 2/10 422/24 |
| 2004/0244138 A1 | 12/2004 | Taylor et al. | |

OTHER PUBLICATIONS

Kobo Utility Corporation, UVCart, High Speed Disinfection (MA), Jan. 2021, pp. 1-5 (Year: 2021).*
Kobo Utility Corporation, UVCart, High Speed Disinfection (MA), Jan. 2021, pp. 1-5.
Inclean ISSA, Nilfisk Expands Autonomous Portfolio, InClean Magazine, Sep. 18, 2020, pp. 1-6.

* cited by examiner

*Primary Examiner* — Michael Maskell
(74) *Attorney, Agent, or Firm* — BYCER & MARION, PLC; Matthew L. Bycer

(57) ABSTRACT

A utilitarian highly maneuverable mobile disinfection unit for floors and other horizontal surfaces. A stable steerable self-powered cart is provided with an attached downward-projecting UVC light source. The light source has a parabolic reflector projecting the radiation downward and a peripheral floor brush doubling as a shield against escape of radiation.

19 Claims, 6 Drawing Sheets

MOBILE STERILIZATION UNIT

CLAIM OF PRIORITY

The present application includes subject matter disclosed in and claims priority to a provisional application entitled "Mobile Sterilization Unit", filed May 28, 2021 and assigned Ser. No. 63/194,853, describing an invention made by the present inventor, herein incorporated by reference.

BACKGROUND OF THE INVENTION

1. Field of the Invention

The device relates to efficient and safe sterilization of flooring surfaces via exposure to UVC electromagnetic radiation, and particularly as applied via an optimized user mounted mobile unit.

2. Description of Related Prior Art

Cleaning capability of current liquid disinfectants, "mopped" over floor surfaces, attains an approximately 37% kill of pathogens present, and is a sloppy solution that requires saturation of the liquid on the floor surface.

There are many different types of surface cleaners that are configured for use with respect to various surfaces such as, for example, streets, hard floors, and carpet. In the warehouse environment, surface cleaners can be configured as riding or towed-behind units. These surface cleaning machines include surface cleaning components as rotatable scrubbers, which are typically found on carpet cleaners and extractors and hard floor surface cleaners, as well as rotatable sweepers, which are typically found on street or floor sweepers, for example.

Although such surface cleaners may provide excellent results, some environments (e.g., hospitals, food processing plants, etc.) require additional efficiency and thoroughness to be made to ensure sanitization of the surface being cleaned. In such instances, the surface cleaners may apply a chemical disinfectant to the surface. Typical cleaning chemicals can be hazardous, requiring the user to take safety precautions before handling the chemicals, and special care in their disposal. Therefore, the use of such chemicals can be dangerous, time consuming, and expensive.

In some locations, scrubbing and chemical disinfection are not enough, and application of IV disinfection technology is desirable. The germicidal qualities of UV light, and particularly the UVC wavelength, have been well established. Examples of self-propelled UV sanitization devices have combined with scrubbing/sweeping components, as well as a walk-behind floor sweeper and sanitizer and a handheld UV sanitizer. Many employ a towed UV light apparatus for sanitizing artificial turf surfaces, combined with tines and brushes to position the blades to receive the light waves are also known in the art.

There is a need for a compact user mounted mobile sterilization unit that can efficiently and safely apply UVC light to sanitize a mostly horizontal floor or surface. Mounting a sanitizer to the front of the unit for accurate tracking and UVC intensity sufficient for single pass sterilization are preferable.

It is therefore a primary object of the present invention to provide a mobile sanitizing unit capable of achieving significant pathogen neutralization.

This and other objects of the present invention will become apparent to those skilled in the art as the description thereof proceeds.

SUMMARY OF THE INVENTION

The present device described is directed to a self-powered forward attachment to a user-mounted vehicle which effectively kills Bacteria. Spores and Virus (including SARS-Cov-2, the coronavirus responsible for COVID-19) by producing an intense UVC germicidal light.

A user mounted mobile sterilization apparatus includes a wheeled vehicle with a UV radiation unit configured to direct UVC light downward toward a flooring surface. In a preferred embodiment, the radiation unit comprises a curved or parabolic reflector with an optimized reflective surface, one or more UVC lamps, a portable power source and specially configured multipurpose brushes along the periphery of the unit. The unit includes a user-mounted vehicle with a forward positioned cleaner.

A highly maneuverable and stable small sized motorized four-wheel vehicle mobile driven sterilization unit provides radiation treatment towards a flooring surface. The unit includes a cart with a frame set on a pair of rear and forward wheels. The user controls the unit steering via a steering assembly which includes a steering column or post which is canted forwardly to assist in balance fore/aft. User sits on a seat assembly, as described and shown below. A first drive battery is mounted on or within the frame to power a drive motor coupled to at least one of the wheels/axles. A first forward compartment is set in front of the steering post. A second forward compartment may be set in front of the first compartment. One of the forward compartments houses a second battery, and optionally an electric DC to AC transformer. Preferably, the battery is directly connected as a power source to the ballast, with the ballast directly wired to the DC battery power, no inverter or transformer needed. An irradiation/sanitizing light box is positioned at the front and is coupled to the frame via a bracket. The light box is electrically coupled to the second battery. The light box may be mounted to the cart via a bracket set at the height of the front axle, with a cart bumper positioned rearward of the light box. The bracket may be positioned at a height of said front axle.

The lightbox is preferably a cuboid frame having a solid top wall, and four solid side walls with an open bottom, the open bottom exposing the interior to the flooring surface. The bottom is preferably framed around its perimeter with a brush system. A curved reflective sheet is set within, and towards the top/sides of the light box to reflect light in the interior space until it exits out the bottom at a myriad of angles in three-dimensional space, or is otherwise absorbed by the reflective sheet or components (e.g., screw heads, structural interior frame, etc.) or the brush. The frame and components may be coated with reflective and/or static-proof coatings. An interior gasket may be set within the perimeter to reflect light rays that would otherwise be directed into the bristles. Light comes directly to the floor from the bulbs, and reflected on the interior surfaces within the light box. Light also reflects from the flooring surface, off the reflective sheet and is exposed to the flooring surface. Bulbs provide a light source within the reflective interior space. The bulbs preferably draw power from the second battery through ballasts. The lights are preferably positioned near a focus point of the curved reflective sheet, and preferably at least three inches above the ground. The light source or bulb is preferably one or more light bars positioned horizontally in parallel along the reflective sheet, and preferably provides light in three-hundred-and-sixty-degree arc (in a single plane, but otherwise in all directions) along much of the length of the bar. The bulbs may include at least a pair of light bars arranged in an interleaved array.

The bristle skirt set is around a lower perimeter, and may be made of (or a plurality of) bristles, wherein each of (or a majority of) the bristles has a top end coupled to said light box and a lower end in contact with the flooring surface. Preferably, a second bristle skirt is set along the lower perimeter nested within and along the outer bristle skirt. A static strip may be set along the lower perimeter between the two skirt rows and in physical or electrical contact with the bristles or base support of the bristles.

A motorized mobile driven sterilization unit may simply include a cart with four wheels, with a first power source within the cart coupled to a drive motor, and a second battery in a forward compartment. A light box is positioned at the front electrically powered by a battery in a forward compartment (rear of the light box). The light box includes an interior with a curved reflective sheet defining a reflective interior space mounted in the cuboid frame of the light box. One or more light sources may be set within the reflective interior space. A bristle skirt may be needed and would be set around a lower perimeter of the light box, preferably reaching the floor. The bristle skirt preferably extends laterally beyond the lower perimeter and extends beyond a mating point with an adjacent skirt length and overlaps the adjacent skirt at one, two, three, or all four corners.

The steering assembly allows for turning the front wheels. A post or column may raise a set of handle bars, the post canted forwardly. Preferably, the location, height and angled orientation of each of the seat assembly and steering assembly cause a driver's center of balance to rest between the handle bar(s) and a seating point on the seat.

DETAILED DESCRIPTION OF THE PREFERRED EMBODIMENTS

Figure 1:
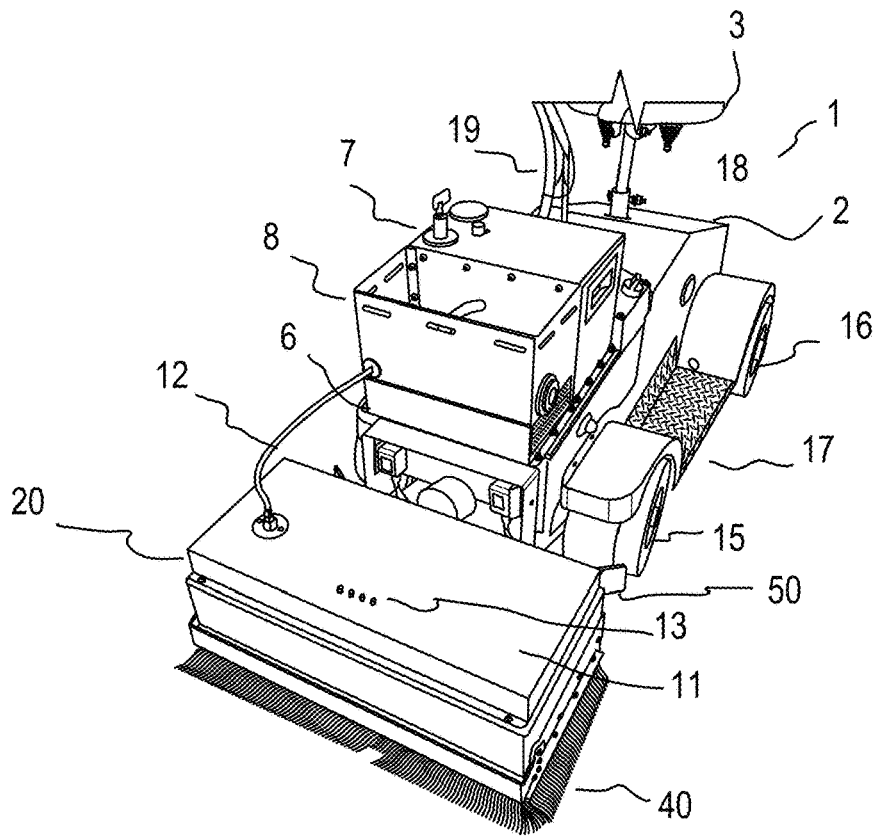
FIG. 1 shows a top perspective view of an embodiment of a mobile sterilization unit of the present invention.

The present invention is an improvement on self-ride vehicles that are mobile, agile, and user-friendly. The present invention builds on work conducted by William M. Lawson, Jr. to provide a safe, reliable, and stable, and maneuverable mobile vehicle as described in U.S. Pat. No. 6,860,512, issues Mar. 1, 2005 entitled "Utility Motor Vehicle With Carrier" herein incorporated by reference.

Utilizing a similar four-wheel model with forward leaning steering post, the driver can transfer his/her weight laterally and fore/aft while driving in order to better maneuver the vehicle. The device can be ridden by a user at any speed up to approximately fifteen miles per hour (MPH), but is preferred to move at a slower rate to secure higher irradiation. The UVC light generated by the Metrans' Sanitizer (average output at floor height), travelling at an average of approximately 2.5 mph over the floor surface. This is referred to as the Dose, which has an effective measured disinfection power, or "Log Value" of 2-log or better at floor surface level. The "Log Value" is the measured sanitizing results of applying the Dose to the floor surface. Metrans, through in-house testing, observed a sanitizing level of 2-log (99% clean). The initial cleaning through independent testing is to Log 1 (90%) at 2.5 mph speed. 2-log sanitization (99%) was observed in neutral testing along a second pass. If the Metrans' Sanitizer equipped Vehicle travels slower over a floor surface, or traverses the same floor surface multiple times, the Dose is increased and the Log value (potentially 3-log [99.9% clean]) increases. The dimensions of the UVGI light housing (which translates to the surface area treated with a pass of the Metrans' Sanitizer mounted on the Metrans' Vehicle) is 11" by 23" (for a constant cleaning area of 253 square inches).

Leakage occurs when light rays escape the light box sterilization unit, typically exiting confines along the flooring surface (below the brushes) or out the sides. Therefore, the device is sized and arranged to ensure contact with the bristles with the flooring surface and overlap and redundancy to avoid inadvertent leakage. The Metrans UVC Sanitizer was also submitted to Leakage Testing. The Light Housing was powered up and checked for UVC light leakage around its' perimeter. While there may be occasional small UVC light leakage located at the intersection of the floor sweeping brushes attached to the light housing, Metrans' test results did not indicate that any bystander would be subject to potentially harmful amounts of UVC light exposure. Additionally, due to the effectiveness of the floor sweeping brushes in shielding potential leakage of UVC light, measurement of potential leakage was so minor that potential exposure of the Operator of the Metrans' Vehicle equipped with the Metrans' UVC Sanitizer was virtually nonexistent, thereby not limiting the duration of operation of the Vehicle and Sanitizer.

The light unit is preferably powered by a separate power source than the power source during the vehicle. A preferred power source is a nominal 24-volt 50 Ah lithium-ion battery to supply power to the lighting system. Initial testing of the Metrans' Sanitizer has resulted in an observed average "duty cycle" (run time on one battery charged at "Full Charge") of approximately 6.5 hours, with a recharge time (when fully discharged) with the provided on-board battery charger of approximately 2 hours. The on-board 24-volt DC LiPo (lithium-ion polymer) battery has no memory and can be partially recharged when discharged to 20% from any 110/115/120-volt wall outlet. A further/alternate preferred power source is a set of four 12-V, 23Ah sealed lead-acid (AGM) batteries, wired to 24 volts. In such a manner, the total amp-hours, Ah, from the set of four batteries is 92 Amps. This battery pack will run the bulbs in the sanitizer for approx. six hours, with a recharge time of about one hour with the dedicated, on-board charger.

Figure 2:
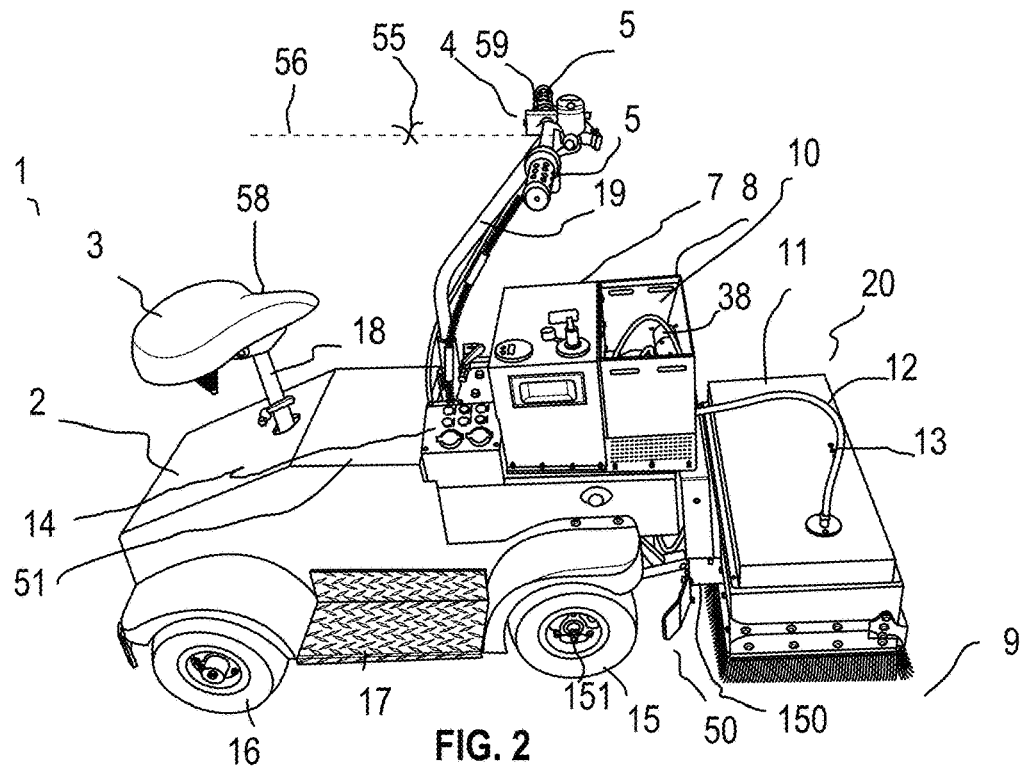
FIG. 2 shows a side view of the unit of FIG. 1.
Figure 3:
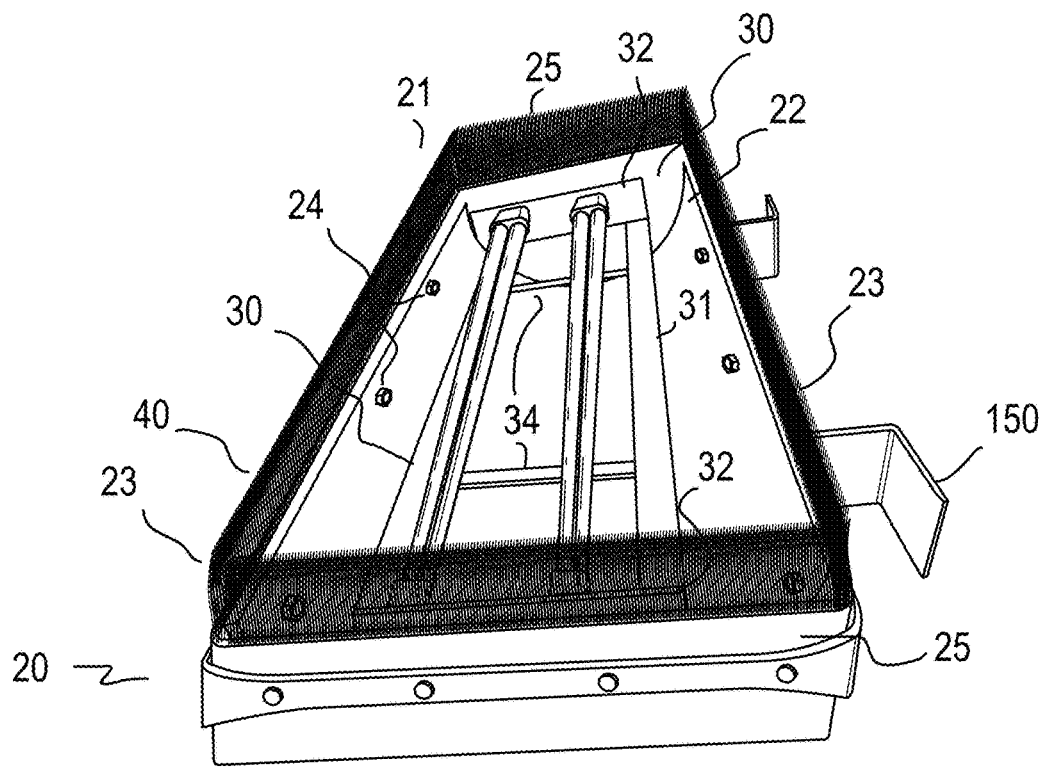
FIG. 3 shows an upside-down lower side perspective view of an embodiment of the inside surface of a light box for use with the present invention.

FIGS. 1 and 2 show an embodiment of the present invention as a user-mounted mobile sterilization unit. Mobile sterilization unit 1 is a four wheeled self-propelled cart 2 with a seat 3, a steering mechanism 4 and operating controls 5 atop a propulsion system and power source (not shown), which may be electric. Seat is preferably of the saddle type, which allows the driver to readily shift his weight while operating the vehicle. Dashboard 14 provides access to on/off switch, other controls and gauges demonstrating operating parameters of vehicle and power to lights. Vehicle cart 2 is preferably supported by a pair of front and rear wheels. Front wheel 15 are arranged with rear wheels 16 (step plate 17 set therebetween) with cart 2 so that the cart has a generally forward-leaning posture. User sits on seat 3 with weight supported at point 58. Seat includes seat post 18, preferably angled backwards from cart 2. Top plate 51 of cart is set along the axis of cart, and therefore is angled slightly downwards 1-25 degrees, or more preferably 2-5 degrees down in front. User further supports self via handgrips 5 on steering mechanism 4. Steering mechanism includes steering post 19 which is angled forward to help generate the user's leaning forward and placing weight on the handlebars at rest. As the vehicle accelerates, the user is drawn to push body weight forward and push on handle bars to support self. A horizontal distance 56 is set between resting point 58 and handle bar weight point 59, with user center of gravity set between point 58 and 59, and preferably near midpoint 56. Battery power source 10 can be charged by pugging into a wall socket via power charging port 38 in the forward compartment 8, shown here on left side.

Light box 20, which provides UVC energy directed downward toward a floor or other surface 9, is attached to the front face 6 of the cart 2. Light box 20 is mounted via mounting brackets 150 to main cart 2, mounting brackets 150 set at the height of forward wheel axle 151, or at least overlap the center of axle height. Separate cuboid compartments 7 and 8 are mounted on top of the front portion of the cart 2. Herein, the term "cuboid" refers to a three-dimensional structure that has six quadrangular sides, each of the opposing sides being a mirror image of its opposite. Similarly, the light box is generally cuboid for the purposes of this disclosure, with an open side roughly equivalent to the opposite top wall. The first compartment 7 is enclosed and contains power source for vehicle, such as a DC battery. The second and forward compartment 8 includes power source 10 for light, such as a Lithium ion, lead acid, or like battery. The forward compartment may be open at the top and provide access to power battery. A nominal 24-volt 50 Ah lithium-ion battery preferably supplies power to a plurality of ballasts, discussed below, which in turn power an equal number of UVC bulbs. Power is transformed via transformer (discussed below) to convert DC to AC power to drive lights. Alternatively, lights may run on DC power. Power cord 12 provides electrical power and communication for commands to lights in light box 20. Light box 20 also include indicator lights 13, such as a line array of lights as shown on top forward of box.

Figure 4:
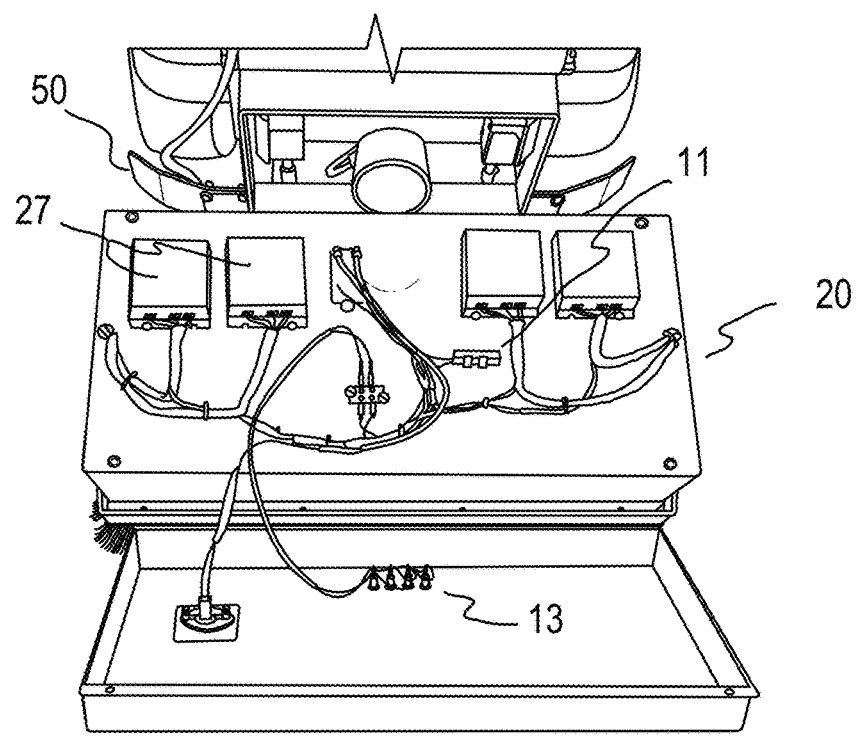
FIG. 4 shows an underside view of an embodiment of a light box for use with the present invention.
Figure 5:
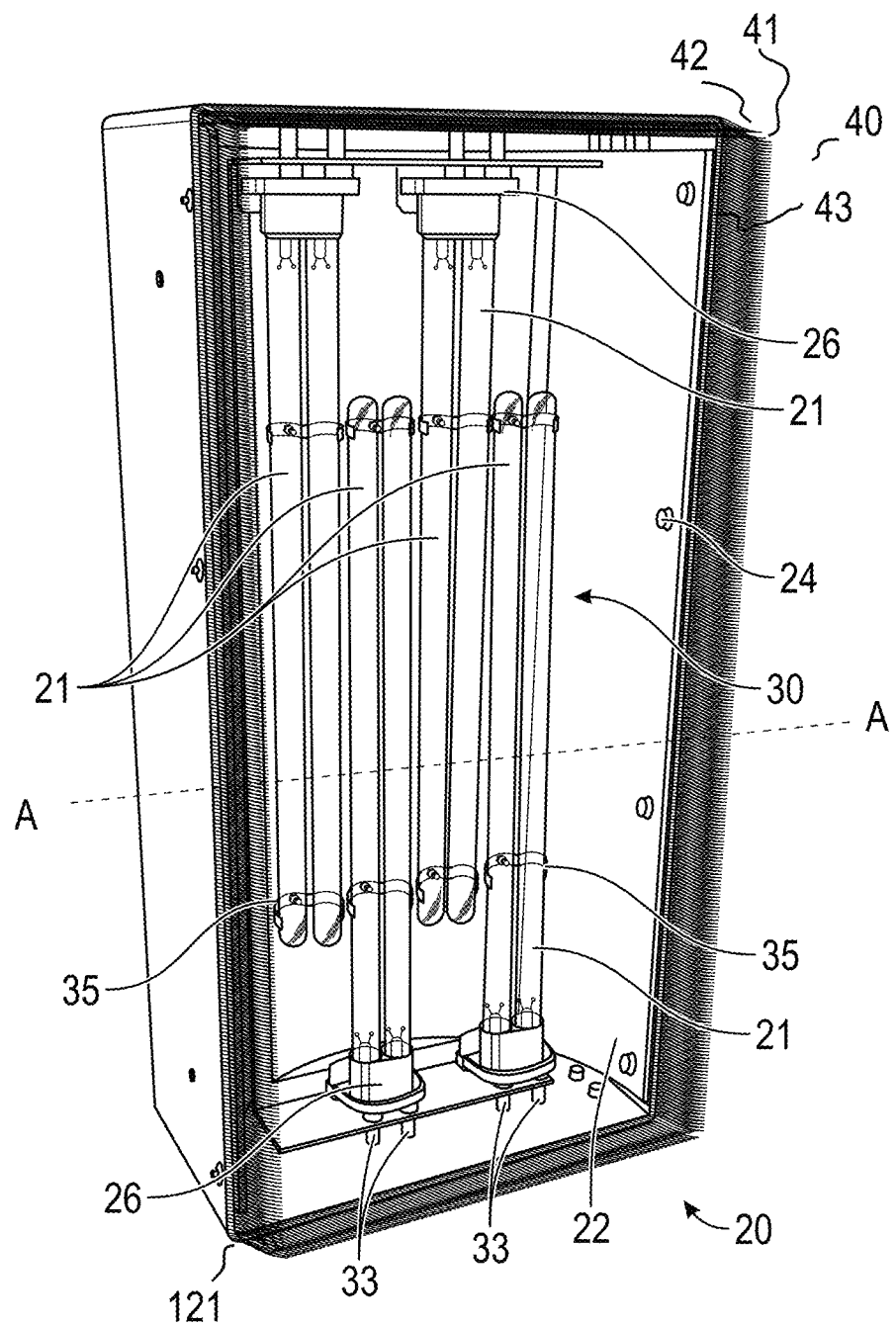
FIG. 5 shows an underside view of a light box for use with the present invention.

Light box 20 is a rectangular box which, in this embodiment, is approximately eleven inches by twenty-three inches by twelve inches deep. The box, as seen in FIGS. 4-6, contains a reflective surface and a plurality of UVC bulbs 21 that provide the disinfection function of the unit. Inside the box is a parabolic reflector 22 that reflects UVC radiation downward toward the treatment surface. The reflector 22 is a high-reflectance white PTFE sheet, such as those available from Thorlabs, Inc. of Newton, NJ for UV irradiation and sterilization. Sheets are approximately 10 mm thick to provide stiffness needed to hold a parabolic shape when it is affixed to the sides 23 of the box using bolts or other fasteners 24. Sheet is preferably arranged in a parabolic or circular cross-sectional shape. The reflector material may be rather prone to static, and is therefore protected with a coating and brushes as set forth below. Other material for the reflector, include HDPE, reflective metal or glass, or other materials known in the art. The use of direct (downward) light and reflected light from reflector in a multitude of directions, allows for comprehensive exposure to lights at flooring surface.

Because the mobile device will generally be travelling on floors in occupied areas, electrostatic attraction of dirt and dust particles to the reflector, thereby impairing reflectivity, is a significant problem. Anti-static coatings are known in the industry, but it is important that the coating itself not materially degrade reflectivity. Experimentation has shown that a coating comprising a mixture of methyl bis(2-hydroxymethyl) cycloalkyl quaternary ammonium nitrates and chlorides, sold as STATICIDE® Concentrate, from ACL, Inc., of Chicago. IL, when properly diluted, affords a 90% reflectivity level of the PTFE reflector 22 under operating conditions. That is, the presence of the coating plus the distribution of particles that attach despite the coating still maintain 90% reflectivity. The determined mixture is 30% water, 60% isopropyl alcohol and 10% STATICIDE®. This is higher than the standard recommended concentration of the product.

Figure 8:
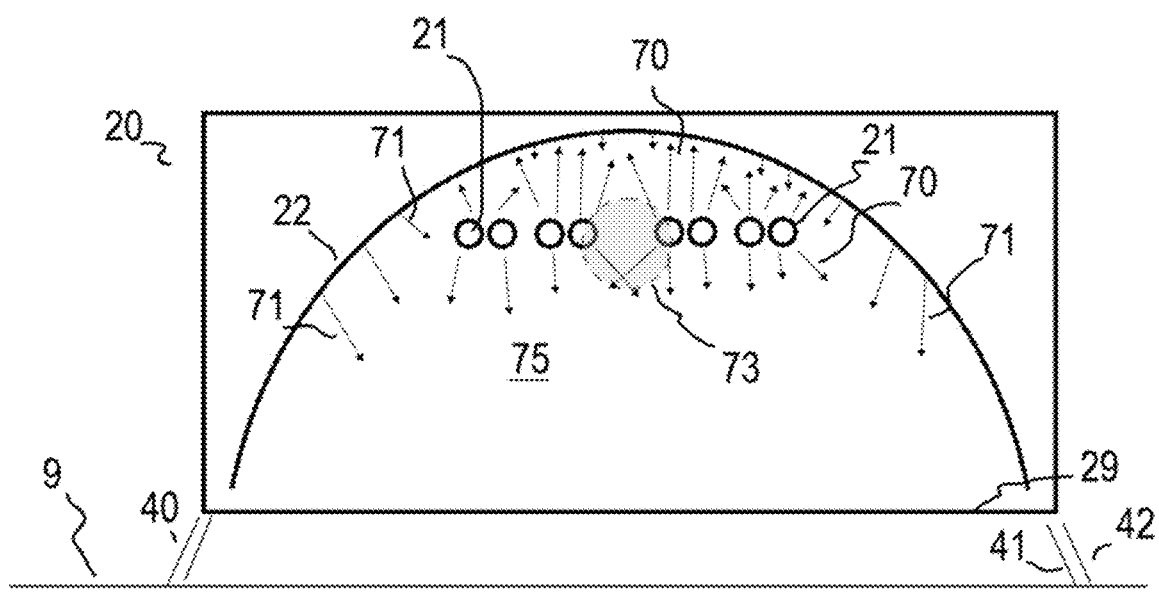
FIG. 8 shows a cross-section of an embodiment of a light box along plane A in FIG. 5.

As noted, the reflector 22 is in a generally parabolic shape. In some embodiments, the reflector may represent a half circular cylinder. For example, see also FIG. 8. In an embodiment, the UVC light source comprises a plurality of UVC tube lights 21 that emit radiation over three hundred sixty degrees in a single plane (in every direction in three-dimensional space). Consequently, much of the radiation is directed away from the surface to be treated and must be reflected back to the surface. The lights are positioned at the approximate line of the latus rectum (a chord perpendicular to the parabola's axis that passes through its focus) of the reflector's parabolic shape, thereby maximizing the percentage of radiation that arrives perpendicular to the surface. In an embodiment, the lights are positioned one to three centimeters from the vertex of the reflector. As seen in FIG. 8, cross-section of light box demonstrates location of bulbs. Light box 20 includes reflector sheet 22 bent into an arc. Light bulbs or light sources 21 (here shown as four dual bulbs) provide light in all three-hundred and sixty degrees, up and down. Light travels, and may include bulbs in the focus area 73 of the reflective sheet. The focus 73 consists of a longitudinal bar or space that extends the width of the light box. Direct light rays 70 leave bulbs 21 and hit reflector 22 at angles relevant to the location of the bulbs, and reflected light rays 71 are directed to the reflector or the ground surface 9. Light also traverses the plane of these cross-section and the ends 25 may also include a light reflecting material. Light travels through the interior space 75 to exit bottom 29 of light box 20. Brush system 40 contains light from exiting the space with interior and exterior 41 and 42 rows. Light hitting the brushes may be scattered and/or absorbed by the bristles.

In a preferred embodiment, the UVC light tubes 21 are TUV PL-L 36 W/4P dual bulbs made by Philips Corporation of Amsterdam. Netherlands. These are compact 110V mercury vapor UVC lamps with a single-side 4 pin connection and available in a variety of lengths. The tubes used in this embodiment are preferably at least one inch long, and more preferably at least six inches long. In preferred embodiments, lights can be up to fourteen inches long or more. An aluminum metal mounting bracket 30 comprising side bars 31 and end plates 32 is affixed at the predetermined height to the ends 25 of the light box 20 using bolts and raised lugs 33. A power socket 26 for each tube 21 is attached to a perpendicular end plate 32 at either end of the frame. Bulb retention clips 35 are attached to cross bars 34 affixed to the side bars 31 Four light tubes 21 are interleaved across the light box, with two plugged into sockets 26 at each end of the mounting bracket 30. Lights may be mounted on either end 25 of light box 20, and interleaved to ensure proper exposure to light throughout the box to flooring surface. The light box is mounted on the mobile unit so that the UVC light tubes are about four to six inches above the floor or other treatment surface.

As noted, power to the UVC tubes is supplied by a 24V 50 Ah lithium-ion battery, preferably separate from any source powering the movement of the cart. A good working battery is the RELiON® RB24V50 lithium iron phosphate battery manufactured by Solarflexion Corp. of Murrieta, CA. The battery connects by cable to an inverter 28 and then to separate ballasts 27 wired to each UVC tube. See FIG. 7. The ballasts may have 24V AC inputs, with power converted from DC battery by transformer 27. Experimentation has shown that a FULHAM® Sunhorse™ Model SHS5-024-C ballast unit, from Fulham Co., Inc. of Hawthorne, CA, works well with the described battery and light tube combination. Bulbs are preferably interleaved, as shown in FIG. 5, with at least one bulb mounted on either side. Shown here are a pair of double bulbs 21 is mounted to sockets 26 for ballast power on either side of box 20. Preferably, the bulbs are mounted also physically into clips 35. The interleaving of bulbs provides for significant coverage on the flooring surface under the light box.

Because UVC radiation is harmful to human skin and particularly to eyes, safety features are built into the mobile sterilization unit to prevent radiation leakage. As seen in FIGS. 8 and 9 a mounted, replaceable brush system 40 extends from the base of the light box 20 to the floor or treatment surface on all four sides of the light box. Two rows of PTFE or Teflon bristles, an inner row 41 and an outer row 42 serve to sweep dirt away and block escape of UV radiation. As further protection against leakage the outer brushes 42 do not abut at corners but extend beyond each other to form an overlap 44. Because electrostatic discharge is a problem in this application, a braided grounding strap 43 such as the tin-plated copper grounding braid available in various widths and thicknesses from McMaster-Carr Supply Company of Aurora, OH. In an embodiment, the grounding strap is approximately one quarter to two inches wide, more preferably one quarter to one-half inches wide, and separates the source of the downward facing bristles. Strip is inserted between the inner and outer row of bristles. Testing has shown that there is no leakage of UVC light through the bristles and only occasional minor exposure at the interface of the bristles and the floor. Thus, no bystander would be subject to potentially harmful amounts of UVC radiation. Moreover, potential exposure to the operator of the unit was virtually nonexistent, there by not limiting the duration of operation of the unit.

Figure 6A:
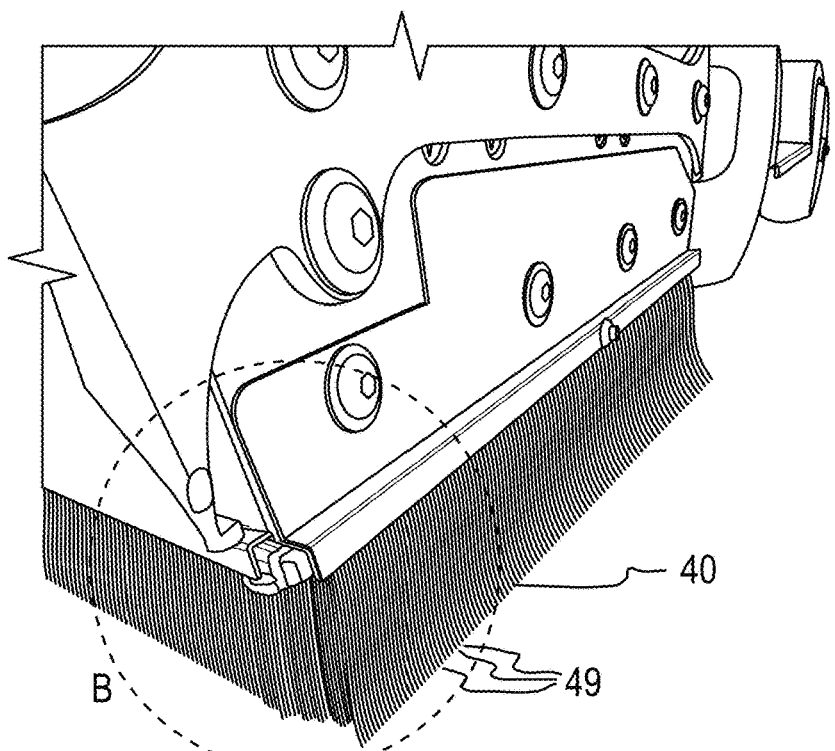
FIG. 6A shows a side view of the lower portion of a light box for use with the present invention.
Figure 6B:
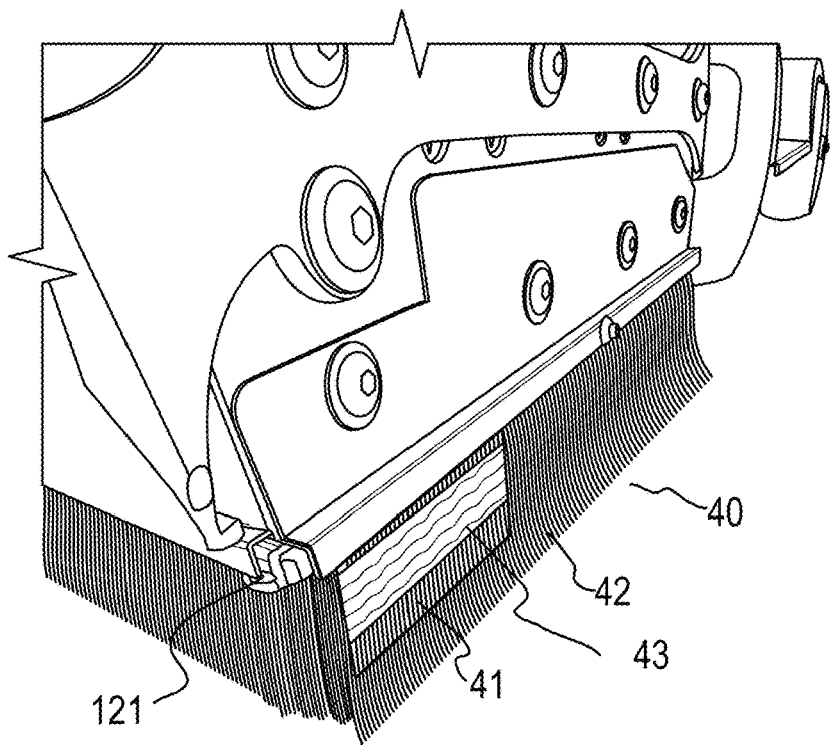
FIG. 6B shows a cutaway view of an embodiment of a brush and static strap for use with the present invention.
Figure 7:
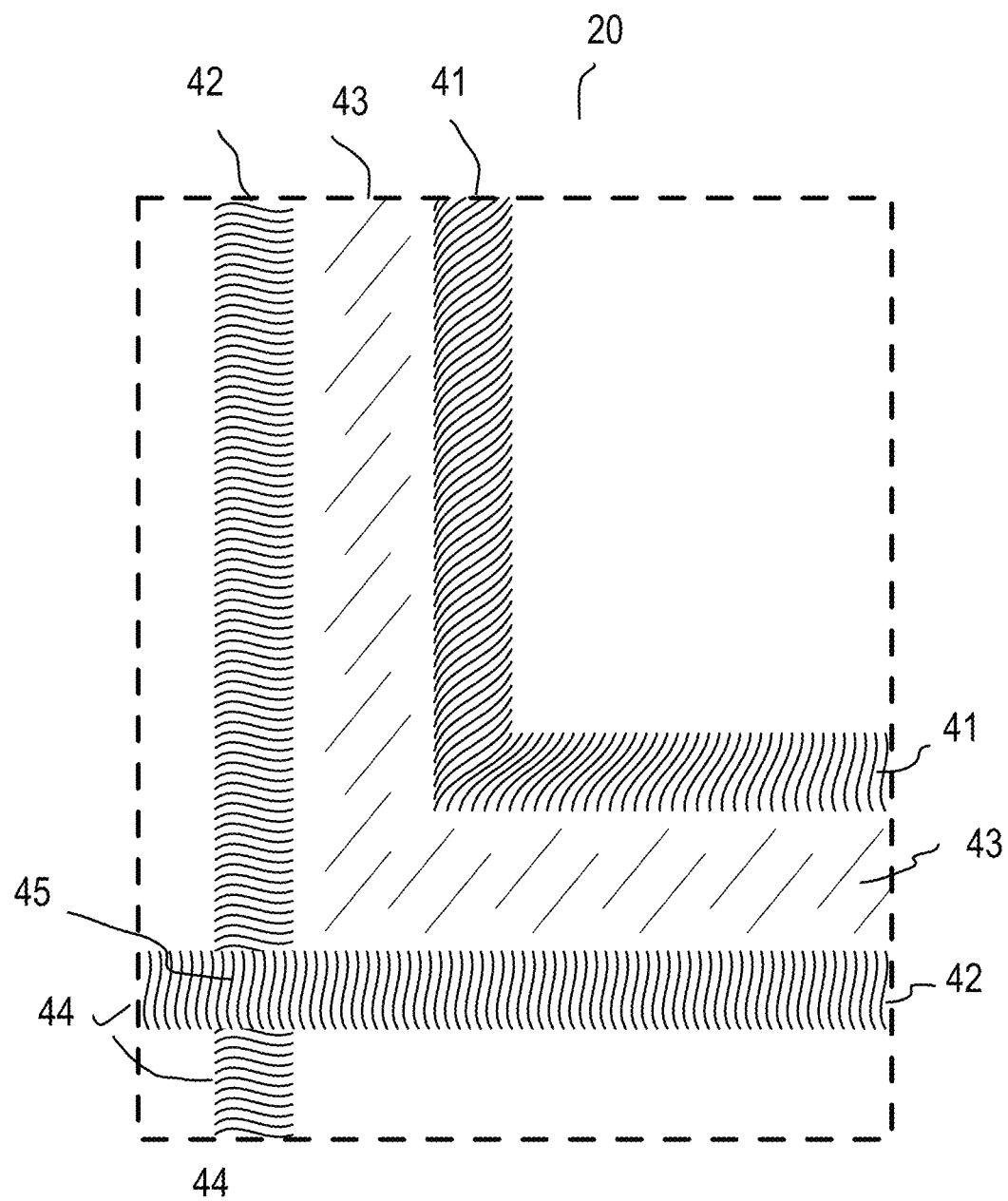
FIG. 7 shows a close-up underside cross-section view of the corner of the light box indicated as circle 13 in FIG. 6A.

Bottom of light box 20 is shown with bristle skirt 40 around the perimeter of quadrangular shaped box 20, as seen in FIGS. 6A, 6B and FIG. 7. Skirt 40 runs the perimeter of the box lower section, with bristles 49 reaching and extending to bend at flooring surface. Each bristle 49 must extend at least the length of the height of box over the flooring surface, if not more so. A 1-5 mm overlength is preferred. Skirt is comprised of a double-row of bristles, including inner row 41 and outer row 42. Attached at the box frame perimeter 47, is strap 43 that acts as a static guard to prevent static from transferring between rows, and also from the bristles to the box itself. The static-guard strap 43 preferably physically contacts the base of each and every bristle to help capture and migrate stray electrons/static from the bristles (picked up at flooring surface) to a ground electrically coupled with main vehicle. At each lower corner 121 of light box 20, the rows of bristles in the skirt 40 overlap to ensure no gaps are found when turning the vehicle. Skirt rows intersect at intersection 45 and include a substantial overlap 44 that extends beyond the confines of the theoretical light box perimeters space to ensure the overlap captures any opening in the skirt and prevents exposure to bystanders.

It is well known that direct exposure to UVGI light is hazardous to the eyes and skin of humans. It is critical that the source of the UVGI light be effectively shielded in order to protect the operator and bystanders from emissions of and exposure to UVGI light. To shield the operator and bystanders from direct exposure to UVGI light, Metrans has incorporated a Sanitizer mounted, replaceable, brush system with virtually eliminates exposure (Tested emission of UVGI light observed at point of contact of floor surface to Sanitizer). Additionally, in the event the Sanitizer is "tipped" or upset in operation, potentially exposing direct UVGI light, the Sanitizer is equipped with a "Tip Switch" which instantly turns off the Sanitizer lamps. Additionally, the Sanitizer is equipped with a master power cut-off switch which provide regular and emergency power cut-off at both the battery pack and the light housing. As an additional precaution, a tip sensor sounds an audible alarm and shuts off power to the lights if the unit diverges more than fifteen degrees from horizontal. Tip switch 11 is preferably located on top of box 20.

The sterilization unit as described has been tested and routinely produces more than 170 microwatts/square centimeter/steradian at the lamp distance from the floor. At that level, with the unit travelling at approximately 2.5 mph over the floor surface, the effective disinfection power is 2-log or better at the floor surface with a second pass. If the unit moves more slowly across the floor, or makes a second pass across the same location, 3-log disinfection may be achieved.

The foregoing description has been presented and is intended for the purposes of illustration and description. It is not intended to be exhaustive nor limit the invention to the above teachings. The embodiments were chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

We claim:

1. A highly maneuverable and stable small sized motorized four-wheel vehicle mobile driven sterilization unit for providing radiation treatment towards a flooring surface, said unit comprising:
   a. a cart with a frame and with a pair of rear wheels and a pair of forward wheels with a front axle for supporting a front wheel at each opposed end;
   b. a steering assembly for turning said front wheels, said steering assembly including a steering column extending up and canted forwardly;
   c. a seat assembly for supporting the rider;
   d. at least a first battery mounted at a location on said frame to power a drive motor to drive one of said front wheels and/or said rear wheels;

e. at least one compartment located forwardly of said steering assembly, said at least one compartment comprising at least a second battery;

f. a light box positioned forward said frame and coupled to said frame via a bracket and electrically coupled to said at least second battery via a cord, said light box comprising:

i. a cuboid frame having a solid top wall, and four solid side walls with an open bottom;

ii. an inverse curved reflective sheet defining a reflective interior space mounted in said cuboid frame;

iii. one or more light sources set within said reflective interior space, said light sources drawing power from said at least second battery; and a iv. bristle skirt set around a lower perimeter of said light box, said bristle skirt comprising a plurality of bristles, wherein each of said bristles has a top end coupled to said light box and a lower end in contact with the flooring surface.

2. The mobile driven sterilization unit as set forth in claim 1 further comprising at least a second bristle skirt set along said lower perimeter of said light box, said at least second skirt nested within and along said bristle skirt.

3. The mobile driven sterilization unit as set forth in claim 2 further comprising a static strip set along said lower perimeter between said bristle skirt and said at least second bristle skirt, wherein said static strip is electrically coupled with along a top end of each bristle of said bristle skirt and said second bristle skirt.

4. The mobile driven sterilization unit as set forth in claim 1 wherein said light source is positioned near a focus point of said curved reflective sheet.

5. The mobile driven sterilization unit as set forth in claim 4 wherein said light source is positioned at least three inches above the ground.

6. The mobile driven sterilization unit as set forth in claim 4 wherein said light source comprises at least one light bar positioned horizontally in parallel with said reflective sheet, said light bar providing light in three-hundred-and-sixty-degree arc along the length of said bar.

7. The mobile driven sterilization unit as set forth in claim 4 wherein said curved reflective sheet includes a forward dip and a rear dip, with a maximal height in the center of the curved reflective sheet, the curved reflective sheet providing a consistent conical cross-section when viewed from the side.

8. The mobile driven sterilization unit as set forth in claim 1 wherein said light source comprises at least a pair of light bars arranged in an interleaved array.

9. The mobile driven sterilization unit as set forth in claim 1 wherein said light box is mounted to said cart via a bracket set at the height of the front axle.

10. The mobile driven sterilization unit as set forth in claim 9 further comprising a bumper mounted to said cart, positioned rearward of said light box.

11. A motorized mobile driven sterilization unit for providing radiation treatment downward towards a flooring surface, said unit comprising:

a. a cart with a pair of rear wheels and a pair of forward wheels with a front axle for supporting each of a pair of front wheels;

b. at least a first power source within the cart coupled to a drive motor to drive at least one of said front wheels and/or said rear wheels;

c. at least one compartment located forwardly of said steering assembly, said at least one compartment comprising at least a second power source;

d. a light box positioned forward said frame and coupled to said frame via a bracket and electrically coupled to said at least second power source, said light box comprising:

i. a box with an open bottom;

ii. a curved reflective sheet defining a reflective interior space mounted in said cuboid frame;

iii. one or more light sources set within said reflective interior space; and a iv. bristle skirt set around a lower perimeter of said light box.

12. The motorized mobile driven sterilization unit of claim 11 wherein said bristle skirt comprises a plurality of bristles, wherein each of said bristles has a top end coupled to said light box and a lower end in contact with the flooring surface.

13. The mobile driven sterilization unit as set forth in claim 12 further comprising at least a second bristle skirt set along said lower perimeter of said light box, said at least second skirt nested within and along said bristle skirt.

14. The mobile driven sterilization unit as set forth in claim 13 further comprising a static strip set along said lower perimeter between said bristle skirt and said at least second bristle skirt, wherein said static strip is electrically coupled with along a top end of each bristle of said bristle skirt and said second bristle skirt.

15. The mobile driven sterilization unit as set forth in claim 12 wherein said bristle skirt extends beyond the lower perimeter and includes an overlap at each of four corners of said lower perimeter.

16. The mobile driven sterilization unit as set forth in claim 11 further comprising a. a steering assembly for turning said front wheels, said steering assembly including a steering column extending up and canted forwardly; and b. a seat assembly for supporting the rider.

17. The mobile driven sterilization unit as set forth in claim 16 wherein the location, height and angled orientation of each of the seat assembly and steering assembly cause a driver's center of balance to rest between a handle bar on said steering assembly and a seating point on said seat assembly.

18. The mobile driven sterilization unit as set forth in claim 11 further comprising a second compartment rear of said at least one compartment and forward of said steering assembly.

19. The mobile driven sterilization unit as set forth in claim 11 wherein said bracket is positioned at a height of said front axle.

* * * * *